(12) United States Patent
Kieffer et al.

(10) Patent No.: US 6,980,625 B2
(45) Date of Patent: Dec. 27, 2005

(54) SYSTEM AND METHOD FOR GENERATING MICROFOCUSED LASER-BASED X-RAYS FOR MAMMOGRAPHY

(75) Inventors: Jean-Claude Kieffer, 3801 av de Melrose, Montreal Quebec (CA), H4A 2S3; Andrzej Krol, Fayetteville, NY (US)

(73) Assignees: Jean-Claude Kieffer, Montreal (CA); The State University of New York, Albany, NY (US)

(*) Notice: Subject to any disclaimer, the term of this patent is extended or adjusted under 35 U.S.C. 154(b) by 0 days.

(21) Appl. No.: 10/227,704

(22) Filed: Aug. 26, 2002

(65) Prior Publication Data

US 2004/0037392 A1 Feb. 26, 2004

(51) Int. Cl.[7] .............................................. H01J 35/32
(52) U.S. Cl. .......................................... 378/37; 378/122
(58) Field of Search ................................... 378/37, 122

(56) References Cited

U.S. PATENT DOCUMENTS

| | | | |
|---|---|---|---|
| 3,961,197 A | 6/1976 | Dawson | 250/493 |
| 4,201,921 A | 5/1980 | McCorkle | 250/493 |
| 4,731,786 A | 3/1988 | MacGowan et al. | 372/5 |
| 4,872,189 A | 10/1989 | Frankel et al. | 378/119 |
| 4,896,341 A * | 1/1990 | Forsyth et al. | 378/34 |
| 5,020,086 A | 5/1991 | Peugeot | 378/113 |
| 5,089,711 A | 2/1992 | Morsell et al. | 250/492.3 |
| 5,151,928 A | 9/1992 | Hirose | 378/119 |
| 5,175,757 A | 12/1992 | Augustoni et al. | 378/120 |
| 5,323,442 A | 6/1994 | Golovanivsky et al. | 378/119 |
| 5,335,258 A | 8/1994 | Whitlock | 378/122 |
| 5,394,411 A | 2/1995 | Milchberg et al. | 372/5 |
| 5,418,833 A | 5/1995 | Logan | 378/154 |
| 5,606,588 A * | 2/1997 | Umstadter et al. | 378/119 |
| 5,712,890 A * | 1/1998 | Spivey et al. | 378/37 |
| 5,812,629 A | 9/1998 | Clauser | 378/62 |
| 5,832,007 A | 11/1998 | Hara et al. | 372/5 |
| 6,094,471 A | 7/2000 | Silver et al. | 378/84 |
| 6,249,566 B1 | 6/2001 | Hayashi et al. | 378/85 |
| 6,324,255 B1 * | 11/2001 | Kondo et al. | 378/119 |
| 6,594,335 B2 * | 7/2003 | Davidson | 378/43 |

* cited by examiner

*Primary Examiner*—Craig E. Church
(74) *Attorney, Agent, or Firm*—Orum & Roth LLC

(57) ABSTRACT

The present invention concerns x-ray sources for mammography. A microfocused x-ray source of small size (30 μm and smaller) with x-ray spectrum optimized for enhanced mammography is obtained with a method and system according to the invention. The proposed x-ray source is based on the use of plasmas created by the energy distribution of suprathermal electrons that are produced during the interaction of the laser beam with a solid target. These hot electrons penetrate the surface layer of cold plasma and interact with the solid core of the target. The method and system according to the present invention allows optimizing the x-ray source size, its spectral distribution, and the conversion efficiency in the 17.3–28.5 keV range (adapted to the breast thickness).

45 Claims, 4 Drawing Sheets

FIG_4

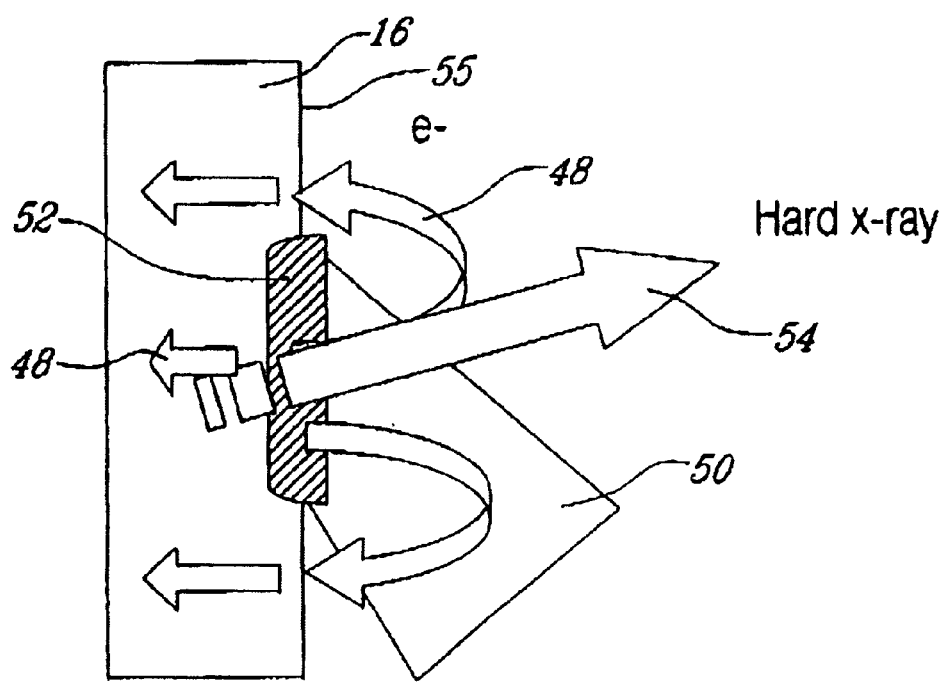
_FIG. 5_
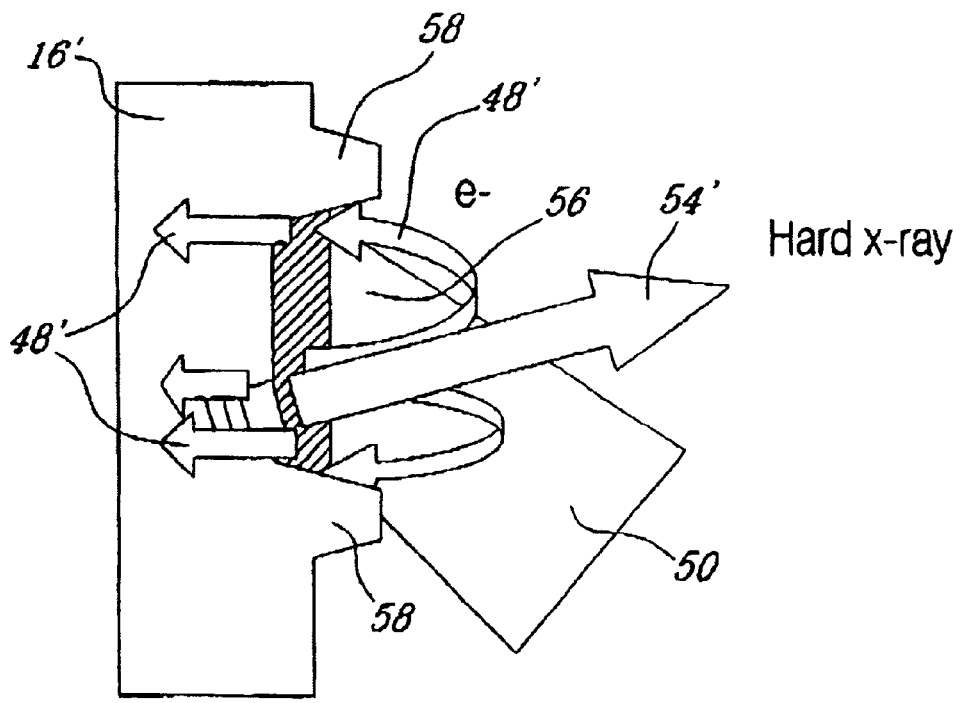
_FIG. 6_

SYSTEM AND METHOD FOR GENERATING MICROFOCUSED LASER-BASED X-RAYS FOR MAMMOGRAPHY

FIELD OF THE INVENTION

The present invention relates to x-rays production. More specifically, the present invention is concerned with a method and system for generating microfocused laser-based x-rays suitable for mammography

BACKGROUND OF THE INVENTION

Mammographic signs of early cancer include calcifications, small masses (densities), neo-densities and architectural distortions. Screening mammography aims at revealing these signs and is highly sensitive and specific. However, still a notable fraction of mammography produces false positive or false negative results These outcomes most occur in the thick and/or dense breast. False positive results may result in an unnecessary additional imaging and biopsy. False negative results, which occur sometimes even when a cancer is palpable, have a severe adverse effect due to delayed biopsy and delayed cancer diagnosis.

Presence of calcifications usually helps to detect breast pathology. Although calcifications demonstrate well-pronounced contrast in mammograms, their detection threshold size is a function of x-ray tube focal spot size, radiographic technique factors including radiation quality, signal-to-noise ratio and exposure time, as well as function of detector and display devices. Even though, in early stages of breast disease microcalcifications are present in approximately half of the cases, they are not apparent on regular screening mammographs before reaching the detection threshold size, which is typically around 100 $\mu$m. This especially applies to punctuate calcifications Some of the inherent limitations of the x-ray tube based screen-film mammography include:
relatively large focal spot (typically nominal ~100 $\mu$m);
varying effective focal spot size across the imaged breast;
suboptimal (below 13 lp/mm) spatial resolution in the upper quadrants for breast thickness above 6 cm:
off-focal radiation;
a relatively low output (especially with microfocus);
a suboptimal spectral characteristic of x-rays for imaging dense fibroglandular tissue and/or thick breast;
restricted latitude of film-screen mammography, and
restricted contrast of film-screen mammography.

Regarding the two last restrictions, film-screen mammography utilizes film as a recording medium to properly record and display relatively narrow dynamic range of x-ray exposures. This should be contrasted with specially designed detectors that can correctly record four orders of magnitude of x-ray exposure. This information can be subsequently displayed on specially designed monitors. Moreover, since film-screen mammography aims at obtaining very high contrast images, the slope of the optical density/x-ray exposure curve is very high. As a result, only a very limited range of x-ray exposure is acceptable If exposure is too high or too low, it will produce exceedingly high or low optical density thus rendering the image not useful clinically.

While the two last restrictions can be alleviated to a great extent by digital mammography, the other limitations stem from the inherent limitations of x-ray tube and are unlikely to be overcome in the framework of this technology.

New technology for generating x-rays had emerged in recent years It relies on emission of x-rays from laser-produced plasma (LPP). This phenomenon occurs when a visible or infrared laser beam is focused onto the surface of solids or liquids If the optical power density exceeds a material dependent threshold value, continuous bremsstrahlung and characteristic x-ray emission lines result. However, initially very expensive and large laser systems were required to obtain the required optical power and the LPP x-ray sources were rather large (100 $\mu$m–1 mm). The invention of chirped-pulse amplification (CPA) in the late 1980's allowed achievement of high optical power density delivered to the target by the laser beam from compact and significantly cheaper table-top terawatt ultra-fast lasers.

The feasibility of CPA lasers for mammography and angiography has been demonstrated in both "High Magnification Imaging With a Laser-Based Hard X-ray Source", IEEE Journal of selected topics in Quantum Electron, Special issue on laser in medicine, 5, 911–915 (1999), by J. Yu, Z. Jiang, J. C. Kieffer, A. Krol. and "Laser-Based microfocused X-ray Source for Mammography faisability Study", Journal of Medical Physics, 24, 725×732 (1997), by A. Krol, A. Ikhlef, J C Kieffer, D. Bassano, C. C. Chamberlain, Z Jiang, H. Pepin, S. C. Parsad. Data in these publications shows the ability to obtain focal spot size of the order of 10 $\mu$m necessary to perform high spatial resolution mammographic imaging and confirm system ability to produce x-ray spectra from a number of different target materials, including Mo, Rh, Ag, In and, Sn with characteristic emission energies spanning 17 3 keV to 28.5 keV.

Even though LLP x-ray source created by CPA lasers can be very small (10 $\mu$m or less) and bright, with peak power many order of magnitude higher than conventional x-ray tubes, a drawback of CPA laser sources from the prior art has been their low average power However, in recent years, significant progress has been made in this respect 20 W average power CPA lasers are presently available, and a 50 W CPA laser is in the design stage.

Finally, there have been studies on sub-picosecond laser-solid-matter interaction devoted to investigation of x-rays generation, from the soft x-rays up to the very hard x-ray emission in the MeV range. However, nobody attempted to simultaneously control the emitted x-ray spectrum, the x-ray source size and conversion efficiency from laser to x-rays.

Method and system for generating microfocused laser-based x-rays allowing to simultaneously optimize the x-ray source size, its spectral distribution, and the conversion efficiency in the 17 3–28.5 keV range is thus desirable.

SUMMARY OF THE INVENTION

An object of the present invention is therefore to provide an improved system and a method for generating microfocused laser-based x-rays.

Specifically an object of the present invention is to provide such method and system allowing optimizing the x-ray source size, its spectral distribution, and the conversion efficiency in the 17.3–28 5 keV range (adapted to the breast thickness and/or density) for improved mammography.

More specifically, in accordance with an aspect of the present invention, there is provided a system for generating microfocused laser-based x-rays comprising an ultra-fast laser; and a solid target with elemental composition positioned in the focal plane of said ultra-fast laser; wherein said ultra-fast laser and solid target are configured so that interaction with said solid target of a laser beam produced by said ultra-fast laser produces suprathermal electrons that penetrate said solid target in a spot whose size is comparable to the ultra-fast laser focal spot size, yielding hard x-rays More specifically, in accordance with another aspect of the present invention, there is provided A method for generating microfocused laser-based x-rays using the above system, the method comprising: without The solid target, generating and amplifying from the ultra-fast laser, a first laser beam pulse train so as to control and adjust the laser energy, positioning the target in the focal plane of the ultra-fast laser so as to offer a fresh surface to the ultra-fast laser; generating and amplifying from the ultra-fast laser, a second laser beam pulse train, and releasing and focusing the second laser beam pulse train on the solid target; whereby the interaction of the second laser beam pulse train on the target generates hard x-rays.

A system and method according to the present Invention allows producing a very small x-ray source with an x-ray spectrum tailored to a specific patient's breast density and thickness suitable to detect pathology in examined breast, for example microcalcifications, with increased sensitivity and specificity, as compared to method and system from the prior-art.

Compared to systems and methods from the prior art, a system and method according to the present invention allows to lower calcification detection threshold size down to approximately 30 $\mu$m, improves visualization of morphology of microcalcifications and marginal characteristics of masses, improves detection of densities (masses), especially in a dense breast tissue, lowers mean grandular dose, especially in a dense and thick breast tissue, and enhances both sensitivity and specificity of mammography.

A method and system according to the present invention yields very small (below 30 $\mu$m) x-ray focal spot size that will results in:

significantly improved and uniform within field of view spatial resolution of the order of 20 lp/mm. In conventional mammography resolution is non-uniform and do not exceed 13 lp/mm. The upper quadrants of thicker (d>6 cm) breasts are imaged with resolution below 10 lp/mm and there is strong gradient of spatial resolution across field of view (in the cathode-anode direction) in the detector plane, better visualization of pathologies, including demonstration of morphology of very small microcalcifications that cannot be imaged with conventional mammography, that will allow earlier detection of breast cancer with significant benefit for women's health; and magnification imaging without necessity of moving breast closer to the source This is necessary in conventional mammography and results in decreased field of view.

Moreover a method and system according to the present invention allows x-ray spectrum to be tailored to specific breast thickness/density that will result in:

lower dose to thicker/denser breast with better contrast, as compared to conventional mammography. Dose saving can be as large as factor of three for very thick/dense breast (d>>4.5 cm); and better imaging of thicker/denser breast due to shorter imaging time. It might completely eliminate "white mammograms" presently obtained with radiopaque breast.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

In the appended drawings:

FIG. 5 is a schematic view illustrating the laser-solid interaction as provided by the x-ray mammography system from FIG. 1 using a flat target, and FIG. 6 is a schematic view illustrating the laser-solid interaction as provided by the x-ray mammography system from FIG. 1 using a shaped target

DESCRIPTION OF THE PREFERRED EMBODIMENT

Figure 1:
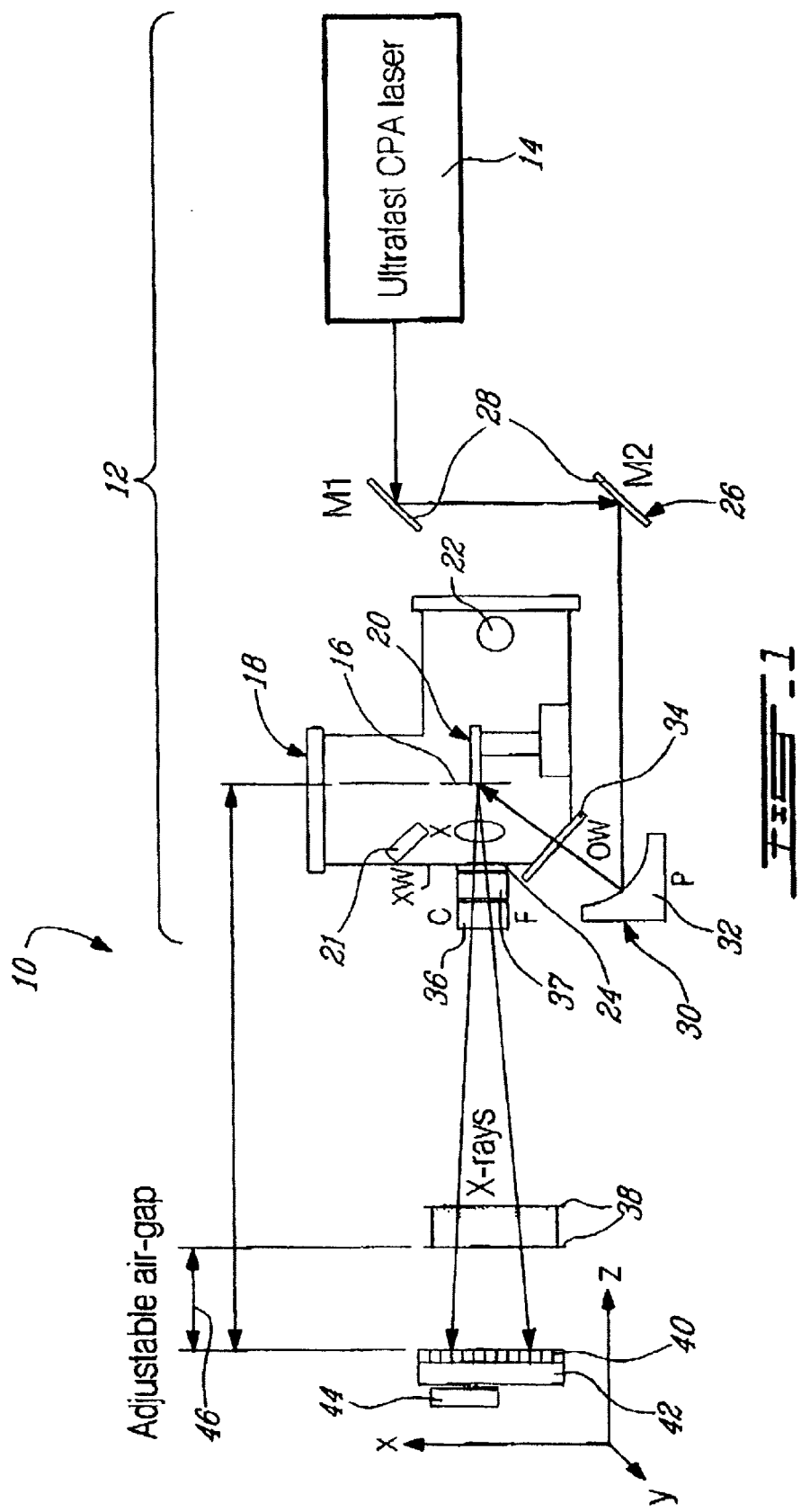
FIG. 1 is a schematic view illustrating an x-ray mammography system including a system for generating microfocused laser-based x-rays according to an embodiment of the present invention.

Turning to FIG. 1, an x-ray mammography system 10 incorporating a system for generating microfocused laser-based x-rays 12 according to embodiments of the present invention are illustrated.

The x-ray generator 12 is based on both a stationary ultra-fast CPA (chirped-pulse amplified) laser 14 and a solid target 16 with elemental composition so positioned as to be in the focal plane of The laser 14.

As it will be explained hereinbelow in more detail, the ultra-fast laser 14 and solid target 16 are chosen and configured so that interaction of a laser beam produced by the ultra-fast laser 14 with the solid target 16 produces suprathermal electrons that penetrates the solid target 16 in a spot whose size is comparable to the ultra-fast laser 14 focal spot size. This allows simultaneously optimizing the source size, the x-ray yield and the photon energy.

The target 16 is mounted in a movable target chamber 18 provided with rapid target/filter changer (not shown), a precision target positioning system 20, a target position monitor and feedback system 21, a target ablation products removal system (not shown), and a vacuum pump 22 for providing vacuum condition in the chamber and more specifically on the target surface. The target chamber 18 allows to precisely positioning a selected area of the target 16 relatively to an x-ray window 24. The x-ray window is located so as to allow hard x-rays produced by the laser-target interaction out of the target chamber in the direction an image receptor 40 as it will be explained hereinbelow in more detail. The movable target chamber allows obtaining all views required in mammography including cranio-caudal view (CC), the medio lateral oblique view (MLO), the latero media (LM), the medio lateral (ML) and supplemental views.

The target/filter allows to properly shape the x-ray spectrum A precision target positioning/feedback allows to keep the x-ray focal spot small.

The precision target positioning system 20 allows mounting and moving, including translation and rotation, the target 16 for reason explained hereinbelow. The target position monitor and feedback system 21 helps precisely position the target relative to the laser focal point and x-ray window 24

As will be explained hereinbelow, the target is to be moved between laser shots so as to expose for each new shot a fresh surface thereof. Since precision positioning systems, and target position monitor and feedback systems are believed to be well known in the art, and for concision purposes, they will not be described herein in more detail.

The x-ray window 24 is preferably made of beryllium. Of course other type of x-ray window may alternatively be used such as Kevlar thin foil.

Of course, the target chamber 18 includes other structures, mechanisms and electronics required for the operation and interactions of the above-mentioned component as it is commonly known in the art. Other features of the movable vacuum target chamber 18 will become more apparent upon reading the following description.

The x-ray generator 12 also comprises an optical beam transfer system 26, coupling the stationary ultra-fast CPA laser 14 and the movable target chamber 18.

The optical beam transfer system 26 includes adjustable mirrors 28 and an optical beam-focusing device 30. The optical beam-focusing device 30 advantageously includes optical feed back system (not shown) for stable laser beam aiming at the target 16, and an adjustable parabolic mirror 32. The vacuum target chamber 18 includes an optical window 34 allowing a laser beam focused by the parabolic mirror 32 to enter the chamber 18 and hit the target 16. The optical window 34 is chosen so as to be transparent to the wavelength of the laser 14 and is advantageously made of MgF. Other suitable transmitting material can also be used. The flat and parabolic mirrors 28, 34 are obviously provided with appropriate mounts (not shown).

Of course, the optical beam transfer system 26 may alternatively have other configurations than the one depicted on FIG. 1. For example, the CPA laser 14 may be positioned so that its beam directly aims at the target 16, with the target positioned at the focal point of the laser 14.

The target chamber 18 further includes a set of filters 36 that are mounted to the x-ray window 24, and an x-ray collimator 37. They allow to properly shape the x-ray spectrum and the x-ray field of view to maximize the image contrast within constrains imposed by the maximum allowable glandular radiation dose and the maximum exposure time.

The x-ray mammography system 10 further includes conventional compression paddles 38 for breast, an image receptor 40 optionally provided with removable mammographic grid 42 allowing for contact magnification imaging, and an automatic exposure and target selection control 44. The automatic exposure control is well known in conventional mammography and is used to avoid over- or under-exposure of the imaged breast. The automatic target selection allows perfect match of the x-ray spectrum and a specific patient's breast thickness/density, resulting in the best contrast at the lowest dose Conventional mammographic x-ray units typically use Mo target Some units have an additional Rh target but the maximum load (mAs) for Rh is significantly constrained, as compared to Mo, and Rh is used infrequently. The image receptor 40 is a mammographic film/screen combination or a mammographic digital detector.

The compression paddles 38 are located between the image receptor 40 and the target chamber 18, and are movable (represented by double-arrow 46 on FIG. 1) so as to advantageously yield an adjustable air-gap between the paddles and the image receptor 40. Very small x-ray focal spot size allows the possibility to perform mammography in a full field of view magnification mode with the air-gap acting as anti-scatter device and without necessity to move imaged breast closer to the x-ray source Thus, it is possible to simply move away the image receptor from the breast while keeping breast at the same distance from the x-ray source as in the contact mammography (e.g. 65 cm), and obtain good quality magnified images. In conventional mammography only spot magnification (i.e. with very small field of view) images might be obtained and the imaged breast has to be positioned much closer to the source (e.g. at 40 cm), as compared to contact technique (e.g. 65 cm).

The image receptor 40 may take many forms such as a mammographic film/screen combination or a digital detector. Since digital detectors and mammographic film/screen combination are believed to be well known in the art, and for concision purposes, they will not be explained herein in more detail.

Of course, the x-ray mammography system 10 also includes other well-known non-illustrated components such as optical and x-ray shielding for operator and patient protection, and a system diagnostics.

The operation of the x-ray generator 12 will now be described in more detail.

Without target 16, a first sequence of high voltages is triggered for the generation and amplification of a first laser beam pulse train in order to control and adjust the laser energy.

The target 16 is then positioned in the focal plane of the optical beam.

It is to be noted that the motion of the target (rotation and or translation in a fixed plane) is triggered in order to offer a fresh surface at every laser shot.

A second sequence of high voltages is then triggered for the generation and amplification of the interacting laser beam pulse train with appropriate energy and pulse number. The pulse number is selected using an adjustable gate.

The pulse is compressed in an optical compressor composed of a set of gratings and mirrors. The shutter is opened at the compressor exit to release the pulse train on the target 16. The laser pulse 50 (see FIG. 5) is of course focused onto the target 16 by means of the parabola 32.

Hard x-rays 54 are produced during the interaction laser beam-target interaction.

Turning now to FIG. 5, the laser-target interaction is schematically illustrated.

FIG. 5 illustrates the laser-solid interaction for the flat target case. In this example, the focal spot size is about 3 $\mu$m in diameter and the incidence angle of the laser beam 50 hitting the surface 16 is 45°. The hatched area represents the 2D slab 52 of thermal plasma generated via radiation pressure confinement.

The angle of incidence of the laser pulse 50 on the target 16, the laser polarization and the target 16 are so chosen as to match the density gradient scale length set by the radiation pressure confinement. Under these conditions, the resonance absorption mechanism that is at the origin of the hot electrons 48, and thus the energy transfer from the laser 14 to the hot electron population 48 is optimized As the resulting plasma is a thin two-dimensional slab (as illustrated in FIG. 5) or three-dimensional droplet (not illustrated) (gradient scale length smaller than the laser beam focal spot size), the trajectories of the hot electrons 48 are limited to the laser focal spot, which can be as small as a few micrometers The electrons 48 penetrate the target in a spot whose size is comparable to the laser spot size. The generated hot electron distribution f(e), is Maximilian More specifically:

$$f(e) = AE^{1/2} \exp(-E/kT_H),$$

where $T_H$ is the hot electron temperature and k is Planck constant.

A judicious choice of target geometry and composition, of the laser pulse duration, polarization and/or intensity, allows shaping the x-ray spectrum and to maintain and control the hot electron temperature between 10 and 50 keV. The conversion efficiency is drastically reduced for hot electron temperatures lower than 10 keV It has also been found that hot electron temperatures higher than 50 keV induce a degradation of imaging contrast due to the high-energy tail in the x-ray spectrum The emitted x-ray spectrum is composed of continuum bremsstrahlung and discrete emission lines. The $K_\alpha$ lines radiation is dominant over bremsstrahlung and can be used, with appropriate filtering for imaging.

As it will be explained hereinbelow in more detail, the laser 14 is configured for providing sufficiently high-contrast sub-picosecond pulses with peak and average power optimized for the imaging task, i.e. breast thickness, composition and imaging time.

According to the present invention, the radiation pressure of the pulse produced by the laser 14 is used to balance the thermal plasma pressure occurring on the target 16 during the laser pulse. This allows the thermal and hydrodynamic mechanisms tending to spread the plasma to be overcome and thus the plasma size (perpendicularly to the target surface) to remain very small. The trajectories of hot electrons 48 above the target 16 surface are then limited and controlled, thus minimizing the x-ray source size.

The laser parameters are controlled as follows. A very high contrast laser pulse ($10^{10}$ 1), indicative of the intensity peak/background noise ratio, is required to help prevent significant plasma expansion before the arrival of the main pulse The pulse duration is set larger than 300 fs and the laser intensity is selected so as to be in the range $10^{18}$ W/cm$^2$–$10^{19}$ W/cm$^2$. At lower intensity the thermal pressure is dominant and the plasma freely expands during the laser pulse, while at higher intensities the radiation pressure can be so high that plasma profile modification becomes a problem In the optimum intensity range, a still two-dimensional plasma slab 52 having characteristic dimensions of optical laser diameter (typically 3 μm) by thermal penetration depth (typically 0.3 μm) is produced during the laser pulse, resulting in constrained hot electron 48 trajectories above the target surface 55

The control of the x-ray source size imposes utilization of a well-defined narrow intensity range ($10^{18}$ W/cm$^2$–$10^{19}$ W/cm$^2$). It has been found that this intensity range is also the most appropriate one for the x-ray photon energy adjustment to optimize imaging for a given breast thickness/density It has also been found that the energy conversion efficiency ($\eta_k$) from hot electrons into characteristic line emission reaches maximum when the hot electron temperature ($kT_n$) is about 3 times the photon energy ($E_k$) of the characteristic line emission (see FIG. 2) Therefore, the photon energy $E_k$ is adapted to a specific breast thickness, by adjusting the hot electron temperature so as to yield $kT_n/E_k = 3$.

The hot electron temperature can be adjusted by a careful laser intensity control indeed, it has been found through experiments that $$kT_n = \alpha(I\lambda^2)^{1/3},$$

where l is the laser intensity and λ is the laser wavelength. Radiation Confined Plasmas yields $\alpha = 5 \times 10^{-5}$ when $kT_n$ is in keV, l in W/cm2 and λ in μm as deduced from experiments with a 400 fs laser pulse at 0.53 μm wavelength. This yields the following expression for the optimum intensity (corresponding to $kT_n/E_k = 3$)

$$l_{opt} = bE_K^3/\lambda^2$$

Figure 4:
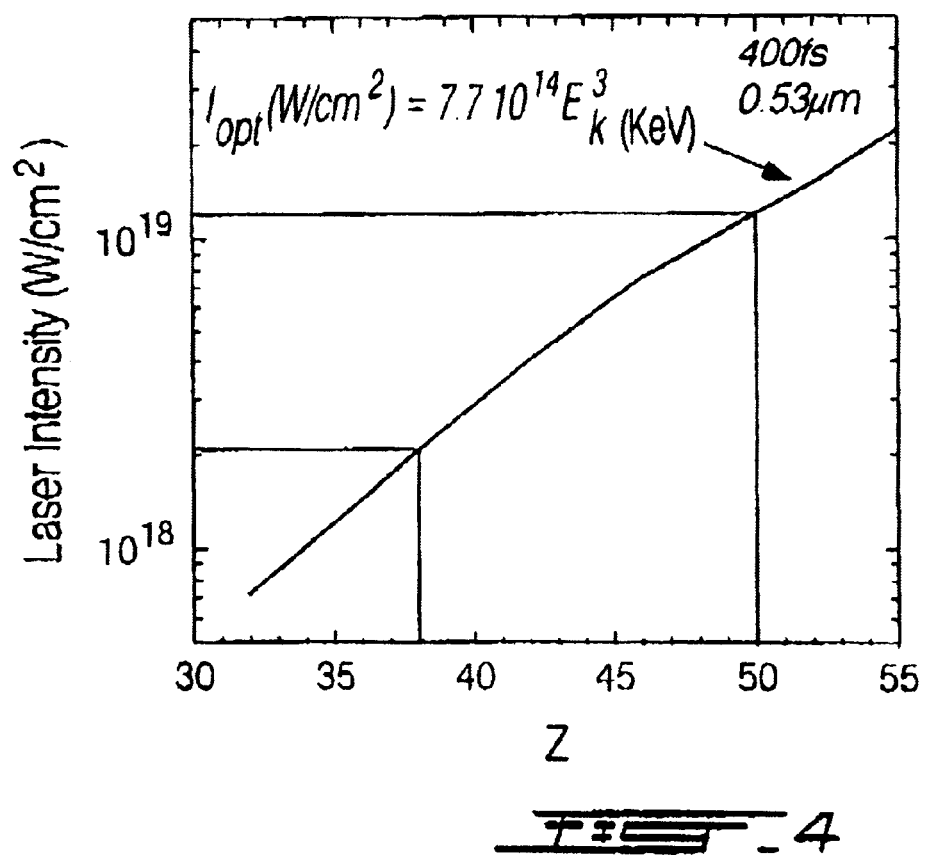
FIG. 4 is a graph illustrating the optimum laser intensity as a function of the target material atomic number Z.

This optimum intensity as a function of the target material atomic number Z is shown in FIG. 4 for a 400 fs laser pulse at 0 53 μm wavelength ($l_{opt}$(W/cm$^2$)=$7.7 \times 10^{14} E_K^3$ (with $E_K$ in keV)). Consequently, energy and yield-optimized x-ray spectra for particular breast thickness and density can be generated by careful selection of both target material and laser intensity.

The laser intensity window, for example, for a laser having a 400 fs pulse and 0 53 μm wavelength, is in the $2 \times 10^{18}$ W/cm$^2$–$10^{19}$ W/cm$^2$ range for production of x-ray spectra suitable for optimized imaging of breast thickness between 2 cm and 8 cm with target atomic number Z between 38 and 50. The use of this intensity range simultaneously allows using RCP and thus controlling the hard x-ray source size;

utilizing targets with the appropriate elemental composition to match the x-ray energy to a patient specific breast thickness/density with an optimized conversion efficiency ($\eta_K$).

It has been found that a pulse duration between 200 fs and 600 fs allows to optimize the plasma confinement effect Through radiation pressure and thus to optimize the x-ray source parameters. Through experiments and calculations, it has also been found that shorter (150 fs) and longer (1 ps) pulse resulted in lower conversion efficiency and/or larger x-ray spot size. According to a preferred embodiment of the present invention, a typical value used for the pulse duration is 400 fs (with no pre-pulse and/or pedestal)

A theoretical investigation of the optimum monochromatic x-ray energy for imaging various simulated pathologies in the breast for a large range of breast thickness spanning the 2-cm–8-cm range was performed. The following figure of merit (FOM) was evaluated $$FOM = (contrast)^2/dose$$

Simulated pathologies included 200-μm calcifications and 5-mm masses.

Figure 2:
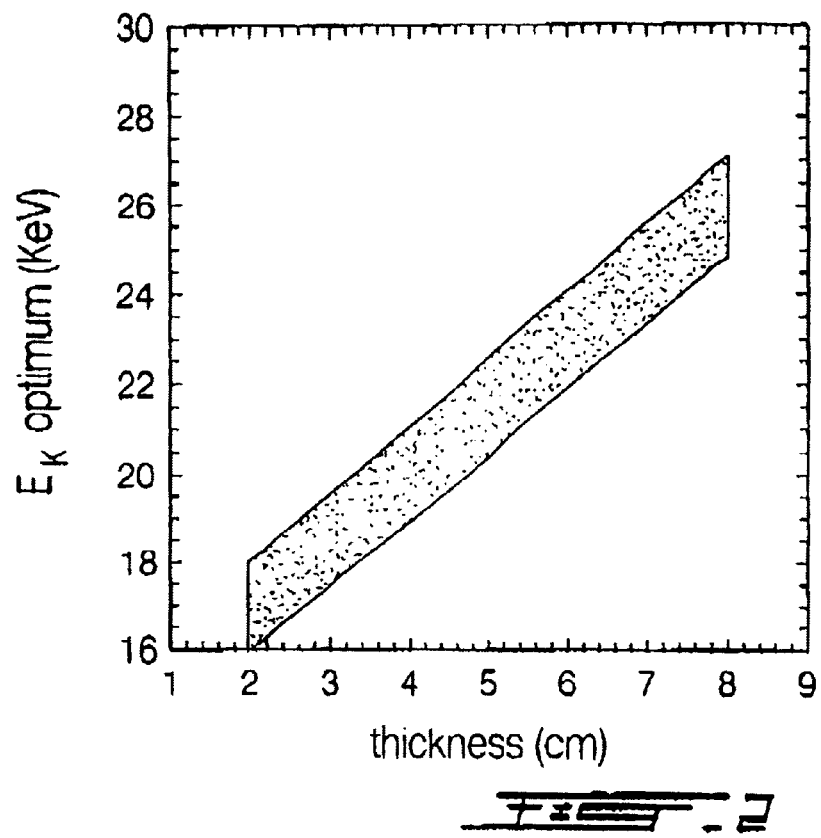
FIG. 2 is a graph illustrating The optimum x-ray energy for imaging various pathologies according to the breast thickness.
Figure 3:
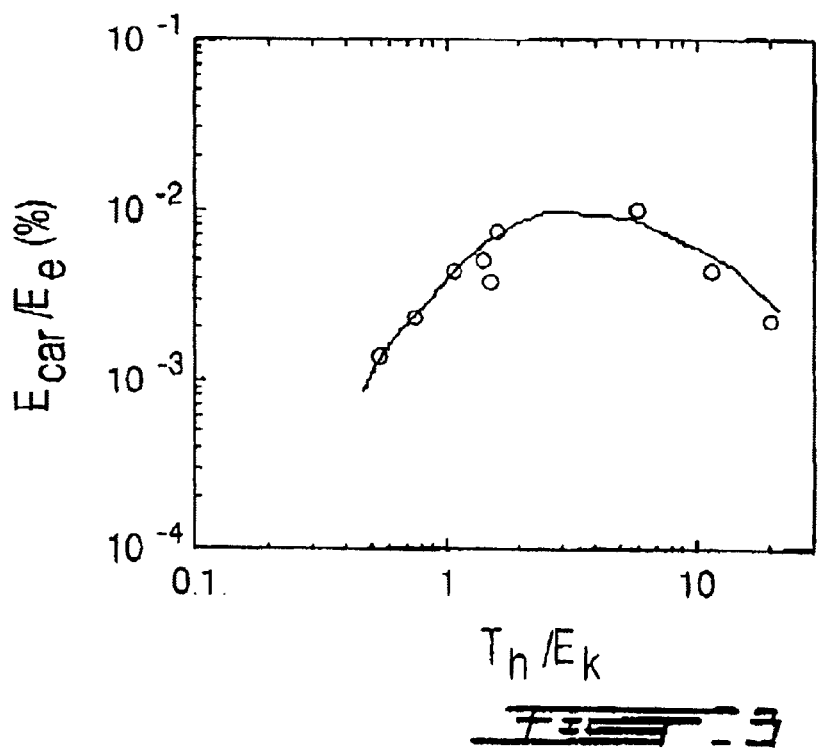
FIG. 3 is a graph illustrating the energy conversion efficiency from hot electrons into characteristic line emission.

It has been confirmed that the shape and the exact location of maximum depend on the imaging object. However in each case the optimum energy shifts towards higher energy for thicker/denser breast for all the investigated pathologies. It has been found that the optimum photon energy increases from ~15–18 keV for 2 cm Lucite equivalent breast to ~25–28 keV for 8 cm Lucite equivalent breast. FIG. 2 shows the calculated optimum photon energy corresponding to FOM maximum as a function of the Lucite equivalent breast thickness For larger breast thickness/density (d>4.5 cm) imaged with ultra-fast-based laser x-ray source, we expect significant improvement in the dose utilization without loss of contrast, as compared to imaging with a mammographic x-ray tube operating at increased kilovoltage (28–31 kVp)

The target 16 can be made in many forms including a continuous thin tape with a plastic substrate, rotating cylindrical or planar solid targets. In any case, the target is rapidly moved between each laser shot so that a fresh surface, with possibly different elemental composition (when required), is exposed to every shot. Possible target elemental compositions include Mo, Rh, Ag, In, Sn, with the $K_\alpha$ lines in the 17 4–27.4 keV range. Via selection of a suitable laser target elemental composition and matching filter 36 material, x-ray spectrum from the LPP x-ray source can be tailored to a specific breast thickness and composition, as well as to a detector used.

Preferably, an x-ray generator 12 according to the present invention includes a shaped target 16' as illustrated in FIG. 6.

In both cases, hot electron 48 trajectories (illustrated in both FIGS. 5 and 6 by full-arrows returning from the slab 52 to into the target 16) are constrained but with flat targets 16 only a fraction of the produced hot electrons 48 is coming back inside the target into a very small spot, producing hard x-rays 54.

As illustrated in FIG. 6, shaped targets produced for example by machine indentation, allows increasing the coupling of hot electrons 48' to the target 16' without increasing The source size. It has been found that the x-ray yield increases when the laser beam 50 interacts with preformed craters 56 (with characteristic dimensions: optical laser diameter (3 $\mu$m) by a laser ablation depth (1 $\mu$m)). The walls 58 of the indentation are capturing electrons that normally escape with a flat target 16 However the shaped target 16' adds a level of complexity since the target 16' positioning has to be controlled with a very high precision level using the precision target positioning system 20.

The operation of the overall x-ray mammography system 10 will not be described herein in more detail since it is believed to be well known in the art Although the present invention has been described hereinabove by way of preferred embodiments thereof, it can be modified, without departing from the spirit and nature of the subject invention as defined in the appended claims.

What is claimed is:

1. A system for generating microfocused laser-based x-rays suitable for mammography, comprising:
    an ultra-fast laser; and
    a solid target with elemental composition, positioned in a focal plane of said ultra-fast laser; said ultra-fast laser and said solid target being configured so that an interaction with said solid target of a laser being produced by said ultra-fast laser produces suprathermal electrons that penetrate said solid target in a spot of a size comparable to a focal spot size of said ultra fast laser; and
    means for matching said solid target and a patient's breast characteristics;
    said system yielding a point source of hard x-rays that enhance a mammographic contrast and minimize a radiation dose to the breast.

2. The system as recited in claim 1, wherein said ultra-fast laser is configured to generate sub-picosecond pulses.

3. The system as recited in claim 1, wherein said solid target is selected from the group consisting of a continuous thin tape with plastic substrate, a rotating cylinder, and a planar solid target.

4. The system as recited in claim 1, wherein said solid target elemental composition is selected from the group consisting of Mo, Rh, Ag, In, and Sn.

5. The system as recited in claim 1, wherein said solid target is a shaped target including preformed craters.

6. The system as recited in claim 5, wherein said preformed craters are formed by machine indentation.

7. The system as recited in claim 5, wherein said craters have a depths of about 1 $\mu$m.

8. The system as recited in claim 1, wherein said solid target is mounted in a target chamber; said target chamber including an optical window transparent to a wavelength of said ultra fast laser for allowing a laser beam produced by said ultra fast laser to enter said target chamber and hit said solid target, and an x-ray window for allowing said hard x-rays out of said target chamber.

9. The system as recited in claim 2, further comprising an optical beam transfer system for coupling said ultra-fast laser and a target chamber.

10. The system as recited in claim 9, wherein said optical beam transfer system includes an optical beam focusing device.

11. The systam as recited in claim 10, wherein said optical beam focusing device includes a parabolic mirror.

12. The system as recited in claim 10, wherein said optical beam focusing device includes an optical feedback system for a stable laser beam aiming at said target.

13. The system as recited in claim 8, wherein said optical window is made of MgF.

14. The system as recited in claim 8, wherein said target chamber further includes filters mounted to said x-ray window.

15. The system as recited in claim 8, wherein said target chamber further includes a collimator mounted to said x-ray window.

16. The system as recited in claim 8, wherein said target chamber is made movable relatively to said ultra fast laser.

17. The system as recited in claim 8, wherein said target chamber is provided with a vacuum pump for providing vacuum condition in said target chamber.

18. The system as recited in claim 5, wherein said target chamber is provided with rapid target/filter changer.

19. The system as recited in claim 8, wherein said target chamber includes a precision target positioning system.

20. The system as recited in claim 18, wherein said target chamber further includes a target position monitor and feed pack system.

21. The system as recited in claim 8, wherein said target chamber includes a target ablation product removal system.

22. The system as recited in claim 8, wherein said x-ray window is made of beryllium.

23. The system as recited in claim 8, further comprising:
    an image receptor sensitive to hard x-rays and optimized for mammography located in front of said x-ray window.

24. The system as recited in claim 23, further comprising compression paddles for breast located between said system and said image receptor.

25. The system as recited in claim 24, wherein said compression paddles are movable so as to yield an adjustable air-gap between said compression paddles and said image receptor and said image receptor is movable so as to yield adjustable source to image distance.

26. The system as recited in claim 22, further comprising an automatic exposure and target selection control.

27. The system as recited in claim 22, wherein said image receptor is provided with removable mammographic grid.

28. The system as recited in claim 22, wherein said image receptor is selected from the group consisting of a mammographic film/screen and a digital detector.

29. A method for generating a point source of microfocused laser-based x-rays suitable for mammography, comprising:
    providing an ultra fast laser;
    generating and amplifying a first laser beam pulse train from the ultra-fast laser so as to control and adjust a laser energy;
    positioning a solid target in a focal plane of the ultra-fast laser so as to offer a
    matching the solid target and the patient's breast characteristics; fresh surface to the ultra-fast laser;
    generating and amplifying, a second laser beam pulse train from the ultra-fast laser; and releasing and focusing the second laser beam pulse train on the solid target;

whereby said releasing and focusing the second laser beam pulse train on the solid target creates an interaction of the second laser beam pulse train on the solid target that generates hard x-rays, said matching the solid target and the patient's breast characteristics allowing enhancing a mammographic contrast and minimizing a radiation dose to the breast.

30. The method as recited in claim 29, wherein said interaction creates thermal plasma on a surface of the target via radiation pressure confinement.

31. The method as recited in claim 30, wherein an angle of incidence of the second laser beam on the solid target, a polarization of the laser and the target are so chosen as to match a density gradient scale length set by the radiation pressure confinement, limiting trajectories of hot electrons produced on the surface of the target to a spot size of the ultra fast laser.

32. The method as recited in claim 30, wherein an intensity I of the ultra-fast laser and a wavelength $\lambda$; are so chosen as to yield:

$$kT_\eta = \alpha(I\lambda^2)^{1/3},$$

wherein $kT\eta$ is a temperature of the hot electrons, and k is the Plank constant and $\alpha$ is a constant.

33. The method as recited in claim 31, wherein $kT_\eta$ is about three times a photon energy $E_k$ produced by the ultra-fast laser, thereby optimizing an energy conversion efficiency from hot electrons into characteristic line emission.

34. The method as recited in claim 31, wherein the intensity I of said ultra-fast laser is optimized using the following equation:

$$I_{opt} = b\, E_K^2/\lambda^3,$$

$E_k$ being the photon energy produced by the ultra-fast laser, and b is a constant.

35. The method as recited in claim 31, where $\lambda$, is 0.53 $\mu$m, a duration of the first and second laser beam pulse train is 400 fs and the intensity I of the ultra fast laser and an atomic number Z of an elemental solid target material are selected according to a graph illustrated in FIG. 4.

36. The method as recited in claim 35, wherein the atomic number Z is selected in a range between 38 and 50 range when the intensity I of the ultra fast laser is in a range between $10^{18}$ W/cm$^2$—and $10^{19}$ W/cm$^2$.

37. The method as recited in claim 29, wherein at least said second laser beam pulse train has a duration selected from a range between 200 fs and 600 fs.

38. The method as recited in claim 30, wherein the spot is about 3 $\mu$m in diameter.

39. The method as recited in claim 30, wherein an electron distribution is Maxwellian.

40. The method as recited in claim 30, wherein the second laser beam is released on the solid target with a 45° angle.

41. The method as recited in claim 30, wherein at least one of a target geometry, a target composition, a second laser pulse duration, and an intensity of the second laser pulse is so selected so as to maintain a temperature of the hot electrons between 10 and 50 keV.

42. The method as recited in claim 30, wherein the plasma is located in a thin two-dimensional slab.

43. The method as recited in claim 30, wherein the plasma is located in a three-dimensional droplet.

44. The method as recited in claim 29, wherein the first laser beam pulse train is a very high contrast laser pulse.

45. The method as recited in claim 29, wherein the first laser beam pulse train duration is larger than 300 fs, and an intensity of the laser is selected in a range between $10^{18}$ W/cm$^2$—and $10^{19}$ W/cm$^2$.

* * * * *